United States Patent [19]

Columbus

[11] 4,426,451
[45] * Jan. 17, 1984

[54] MULTI-ZONED REACTION VESSEL HAVING PRESSURE-ACTUATABLE CONTROL MEANS BETWEEN ZONES

[75] Inventor: Richard L. Columbus, Rochester, N.Y.

[73] Assignee: Eastman Kodak Company, Rochester, N.Y.

[*] Notice: The portion of the term of this patent subsequent to Jan. 12, 1999 has been disclaimed.

[21] Appl. No.: 229,038

[22] Filed: Jan. 28, 1981

[51] Int. Cl.³ .................. G01N 21/03; G01N 33/54; G01N 33/70

[52] U.S. Cl. ...................... 436/518; 138/44; 356/246; 422/58; 422/100; 422/102; 435/4; 435/7; 435/287; 436/98; 436/113; 436/165; 436/177; 436/531; 436/807

[58] Field of Search .............. 23/230 R, 230 B; 422/50, 55, 56, 57, 58, 100, 102, 138; 138/44; 356/246; 436/98, 113, 177, 165, 518, 531, 807; 435/7, 4, 287

[56] References Cited

U.S. PATENT DOCUMENTS

| 2,261,028 | 10/1941 | Hopkins | 138/44 X |
| 2,694,296 | 11/1954 | Prosek et al. | 138/44 X |
| 3,036,894 | 10/1958 | Forestiere | |
| 3,342,600 | 7/1963 | Downey | |
| 3,497,442 | 2/1967 | Vincent | |
| 3,552,925 | 7/1967 | Fetter | 422/56 |
| 3,552,928 | 7/1967 | Fetter | 422/56 |
| 3,619,072 | 3/1969 | O'Hara et al. | 356/246 |
| 3,646,346 | 2/1972 | Catt | 23/230 B X |
| 3,902,964 | 9/1975 | Greenspan | 23/230 B X |
| 3,986,534 | 10/1976 | Schmidt | 422/50 X |
| 4,040,786 | 8/1977 | Trivedi et al. | 422/58 X |
| 4,065,263 | 12/1977 | Woodbridge | |
| 4,088,448 | 5/1978 | Lilja et al. | 23/230 B X |
| 4,162,896 | 7/1979 | Hosli | 422/100 X |
| 4,227,810 | 10/1980 | Sandrock et al. | 356/246 |
| 4,233,029 | 11/1980 | Columbus | 23/230 R |
| 4,310,399 | 1/1982 | Columbus | 422/58 X |

FOREIGN PATENT DOCUMENTS 1037155 7/1966 United Kingdom .

Primary Examiner—Arnold Turk
Attorney, Agent, or Firm—Dana M. Schmidt

[57] ABSTRACT

A reaction vessel, test device, and method of detection or measurement are disclosed, featuring the use of at least two operatively connected zones formed by transport surfaces spaced apart throughout most of the zones a capillary distance. The zones are fluidly connected by meniscus control means effective to stop capillary flow of the liquid from one zone to the other, until an externally generated actuation pressure is applied.

42 Claims, 16 Drawing Figures

COMPARATIVE EXAMPLE

MULTI-ZONED REACTION VESSEL HAVING PRESSURE-ACTUATABLE CONTROL MEANS BETWEEN ZONES

FIELD OF THE INVENTION

The invention relates to a reaction vessel, a test device, and methods of detection or measurement useful in the interaction of liquids and reagents. A preferred use is the measurement of the amount of analytes in liquids.

BACKGROUND OF THE INVENTION

In my previous application Ser. No. 954,689, now U.S. Pat. No. 4,233,029, I describe a liquid transport device formed by opposed surfaces spaced apart a distance effective to provide, through a zone of intended transport, capillary flow of liquid. Once the liquid is introduced into such a device, it continues to flow between the surfaces until either the volume of liquid is exhausted or an edge of the zones is encountered. There is no capability for temporarily stopping liquid flow within a portion of the device, and thereafter resuming the flow, other than by adding more liquid to an exhausted supply of liquid. Temporary stoppage and resumption of flow would be particularly useful for sequential reactions conducted on a constant volume of liquid, such as in an assay of the liquid using sequential reagents separated within the device. The addition of more liquid to cause resumption of flow is not a useful technique when the reaction dictates that the liquid volume or concentration of analyte must remain constant.

Accordingly, what has been desired is a reaction vessel or test device featuring capillary attraction as the means for moving liquid therein, the device being operative to temporarily stop the flow of a given volume of liquid to allow a reaction with a reagent, and thereafter to resume the flow of the liquid for further processing. Such a device would permit immunoassays to be conducted, for example, using labeled antigens or antibodies, and the complementary immunogen as the reagent that reacts (by binding) while the liquid is temporarily stopped. Resumed flow would cause separation of the bound and of the free labeled antigen or antibody into two different zones of the device, permitting accurate detection of the labeled antigen or antibody, and the calculation of the liquid immunogen that is present.

RELATED APPLICATIONS

My U.S. Application Ser. No. 101,662, filed on Dec. 10, 1979, entitled "Liquid Transport Device Containing Means for Delaying Capillary Flow," now U.S. Pat. No. 4,310,399 describes a capillary transport device having means for delaying liquid flow between two regions. The specifically detailed embodiment described therein is one in which the liquid flow rate is retarded, but not significantly stopped, by the delaying means.

SUMMARY OF THE INVENTION

This invention is directed to a multi-zoned reaction vessel and a method for controlling flow from one zone to the other, that permit the use of capillary attraction as the force that moves the liquid. That is, capillary flow between the zones, is temporarily stopped by the configuration of the vessel, in a manner which permits subsequent resumption or reactivation of liquid flow.

More specifically, in one aspect of the invention, there is provided an improved reaction vessel comprising first and second fluidly connected zones, inlet means permitting the introduction of liquid into the first zone, and a passageway connecting the zones. At least one of the zones contains a reagent capable of interacting with a material of the liquid, and the second zone is adapted to receive the liquid from the first zone. The first and second zones comprise a first member, a cover member, and means for disposing the first member and the cover member in superposed relationship, the first and the cover members having opposed surfaces providing transport of liquid introduced between them. The improvement of the vessel results, in part, from the fact that the opposed surfaces are spaced apart a distance that is effective to induce capillary flow of the introduced liquid at least in the portion of the first zone contiguous to the passageway, and in the second zone. The improvement also results from the fact that the passageway includes meniscus control means for temporarily stopping the liquid meniscus from proceeding into the second zone from the first zone. The control means is configured to permit the liquid to flow into the second zone only upon the application to the liquid of an externally generated pressure sufficient to push the meniscus into the second zone.

In an alternate aspect of the invention, the structure forming the second zone has a spaced-apart distance between opposed surfaces that is less than that of the first zone, by a selected amount. The selected amount is effective to preferentially attract the liquid, in response to the push of the liquid by the pressure, into the second zone from the first zone and to confine the attracted liquid within the second zone.

In a further alternate aspect of the invention, at least one of the opposed surfaces comprises, in both of the zones, a relatively non-wettable material coated with a surfactant soluble in the liquid and capable of making the surfaces wettable by the liquid. The effect is that the non-wettable surface material returns to its relatively non-wettable condition after the liquid leaves a given zone, insuring that flow will proceed preferentially to the downstream zone.

In yet another aspect of the invention, the reaction vessel described above is a test device and the reagent of the first zone is (a) immobilized in the first zone, and (b) capable of interacting with an analyte of choice. Immunoassays are possible using such a device, wherein a labeled amount, that is, the analyte analog, is included in the first zone, preferably to compete with the unlabeled analyte of the liquid for a bonding reaction with the reagent. As used herein, "analog" refers to a labeled antigen corresponding to an antigen to be assayed, or a labeled antibody corresponding to a particular antibody to be assayed. Selection of either an antibody or an antigen as the reagent of the first zone serves to immobilize a portion of both the analog and either the patient antigen or antibody, respectively.

In yet another aspect of the invention, the reaction vessel described above permits the analysis of whole blood. The reagent of the first zone is a red cell-agglutinating reagent immovably adhered to the first zone, and the second zone contains a test element including at least one detection reagent specific to the analysis of the analyte of choice. The analyte is detectable from the plasma that is obtained from the first zone following the separation of the red cells in the first zone.

In still another aspect of the invention, a method is provided for interacting a material that is contained in a liquid, with a reagent. The method uses a device comprising two adjacent, fluidly connected zones both of which comprise opposed liquid transport surfaces, spaced apart as described above. At least one of the two zones includes the reagent. The method comprises the steps of (a) filling the first zone with liquid, and (b) retaining the liquid within the first zone while the reagent interacts with the material. Thereafter, the method includes the steps of (c) applying to the liquid in the first zone an externally generated pressure. The pressure is selected to be sufficient to push the meniscus of the liquid from the first zone into the second zone.

Yet another aspect of the invention features a method for detecting the amount of material that is either bound or unbound to a reagent chosen for its capability to bind the material, using a reaction vessel having first and second fluidly connected zones wherein the material and reagent interact in the first zone. The method comprises placing a liquid contaning an unknown amount of the material, in unlabeled form, in the first zone, along with a liquid containing a known amount of the material (the analog) that is labeled for detection, the first zone further including the reagent immobilized therein. The liquid is retained in the first zone while the reagent binds with and immobilizes some of both the labeled and the unlabeled material. The method is completed by applying to the liquid in the first zone an externally generated pressure in an amount sufficient to force the material that has not been immobilized by the reagent to start flowing into the second zone, and detecting the free labeled material in said second zone or the bound labeled material in the first zone.

It is a further aspect of the invention that a method is provided for determining the amount of an analyte of whole blood in a test device comprising two opposed transport surfaces and means for spacing them apart to provide at least two fluidly connected zones. The method comprises the steps of (a) placing a quantity of whole blood within the first of the zones, such first zone containing a cell-agglutinating reagent that is incapable of moving out of the first zone, and (b) retaining the quantity of whole blood in the first zone a length of time sufficient to cause blood cells to bind to the reagent and thus to separate from the blood plasma. Thereafter, the method comprises the steps of (c) applying to the zone containing the plasma an externally generated pressure in an amount sufficient to force the plasma, but not the cells, to flow into the second of the zones, and detecting within the second zone a radiometric change resulting from the interaction between a detection reagent contained in the second zone and the analyte.

Thus, the invention advantageously temporarily stops capillary liquid flow from one zone to a second fluidly connected zone in a multi-zone reaction vessel.

Yet another advantage of the invention is that such stoppage of flow can be overcome by an externally generated pressure which is compatible with the desired processing. For example, the pressure can be applied without altering the liquid volume or concentration and without lysing the red cells of whole blood used as the liquid.

Still other and related advantages feature the use of such a device to analyze whole blood or conduct immunoassays.

Other features and advantages will become apparent upon reference to the following Description of the Preferred Embodiments when read in light of the attached drawings.

DESCRIPTION OF THE PREFERRED EMBODIMENTS

The multi-zoned reaction vessel of the invention is hereinafter described particularly with respect to the measurement or detection of analytes of biological liquids such as serum, plasma or whole blood. Liquids such as industrial liquids are also analyzable using the vessel of this invention. In addition, the vessel can be used to interact a liquid with a reagent for many other purposes.

I have discovered that a reaction vessel wherein intended liquid transport is provided by capillary attraction, can be constructed to temporarily stop the liquid transport, and thereafter reactivate the transport, without altering the given volume of liquid needed for reactions in the vessel. Such a vessel is particularly useful in conducting immunoassays and the analysis of whole blood.

Figure 1:
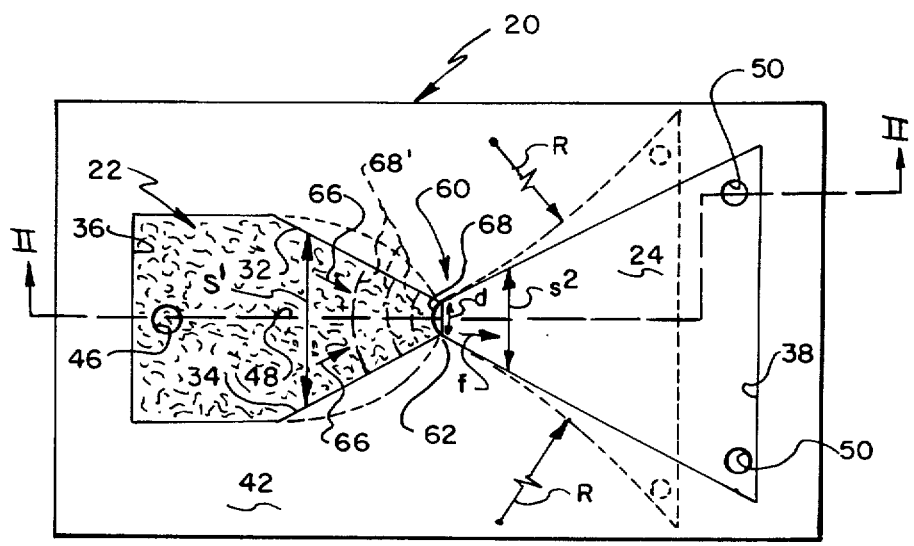
FIG. 1 is a plan view of a reaction vessel constructed in accordance with the invention, showing in phantom certain alternate design configurations.
Figure 2:
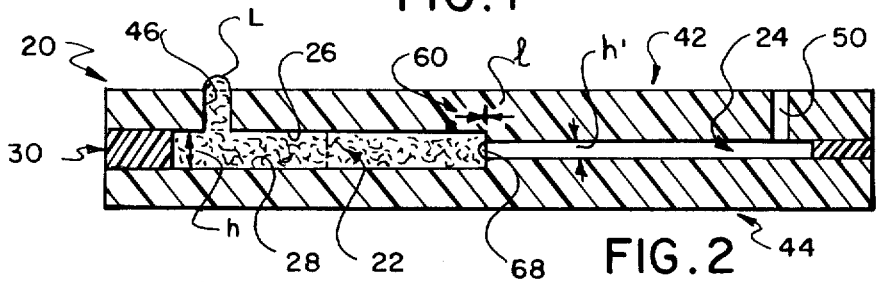
FIG. 2 is a section view taken generally along the line II—II of FIG. 1 and illustrating the first steps in the use of the vessel.

In the embodiment of FIGS. 1 and 2, a reaction vessel 20 is provided, comprising means defining a first zone 22 fluidly connected by passageway 60 to means defining an adjacent zone 24 adapted to receive liquid flow from zone 22. In accordance with one aspect of the invention, the zone-defining means comprise a first member 44 and a cover member 42 disposed in superposed relationship by spacer member 30, FIG. 2. Members 42 and 44 provide two opposed liquid transport surfaces 26 and 28, respectively, and spacer member 30 provides sidewall surfaces 32 and 34 and end walls 36 and 38, FIG. 1. Sidewall surfaces 26 and 28 and walls 36 and 38 are shown as solid lines in FIG. 1 for clarity, such as they would appear if cover member 42 were transparent. Surfaces 26 and 28, FIG. 2, are spaced apart a distance h in zone 22, and distance h' in zone 24, both of which are selected to provide capillary flow of liquid. To insure capillary flow for liquids such as whole blood or blood serum, distance h does not exceed about 1 mm. To complete the transfer of all the liquid into zone 24 following breach of passageway 60, and to retain liquid in zone 24, distance h' is preferably less than distance h. Specifically, a reduction in the spacing distance of at least 25% is useful to induce substantially complete liquid transfer to zone 24 within a time compatible with the analyses of choice. Most preferably, h is 125 microns or less to minimize the amount of liquid required for the reaction within the vessel, and h' is 94 microns or less. The selection of distance h' to be significantly less than h requires that the areas of surfaces 26 and 28 of zone 24 be relatively enlarged to insure that all of the liquid of zone 22 will be accommodated in zone 24.

Additional zones, not shown, lacking such capillary spacing and therefore not adapted to receive liquid flow can be fluidly connected to zone 24, for example, adjacent to end wall 38.

To permit introduction of liquid into zone 22, a liquid inlet aperture 46 is provided in one of members 42 and 44, preferably 42, thereby defining a locus of liquid introduction. A quantity of liquid is to be deposited at aperture 46, preferably in drop form.

The size of aperture 46 is selected to insure that the volume of liquid introduced will contact both surfaces 26 and 28, to initiate capillary transport of a liquid meniscus through zone 22. If a 10 μl of liquid is the amount to be introduced for purposes of the intended test, aperture 46 is preferably about 1.0 mm to about 5.0 mm in diameter. Alternatively, aperture 46 is shaped to have cornered sidewalls, not shown, so as to have the shape of, for example, a hexagon instead of a circle to insure more positive movement of the liquid into the aperture.

To insure proper wave front shape and prevent air entrapment, aperture 46 is located preferably at a point closer to end wall 36 than to sidewall surfaces 32 or 34, FIG. 1. Most preferably, it is located on the bisector line 48 between sidewall surfaces 32 and 34.

In one embodiment of the invention, a reagent (not shown) with which the liquid is to interact in zone 22 is preferably coated or otherwise bonded, such as by a chemical bond, onto any one of the exposed surfaces of zone 22, e.g., surfaces 26, 28, 32, 34 or wall 36. The reagent can be soluble or insoluble in the liquid to be reacted.

To permit air to be expelled from zones 22 and 24 ahead of an advancing liquid meniscus, apertures 50 are provided, preferably through member 42 in the vicinity of zone 24. Most preferably apertures 50 are located adjacent to the intersection formed by sidewall surface 32 with end wall 38, and sidewall surface 34 with end wall 38. Such locations permit full capillary flow in zone 24 with a minimum amount of resistance.

Members 42 and 44 are secured to spacer member 30 by any conventional means, for example, a water-insoluble adhesive.

In accordance with an important aspect of the invention, to control the liquid meniscus by temporarily stopping it from flowing from zone 22 to zone 24, a narrowed passageway is formed by the surfaces defining the zones. In the embodiment of FIGS. 1 and 2, a gradually narrowed passageway 60 comprises sidewall surfaces 32 and 34 shaped to form sharply defined opposed edges 62 located between the two zones and spaced a distance "d". The convergence of surfaces 32 and 34, provided by decreased spacing $s^1$, occurs preferably over at least the last 35% of the flow of liquid within zone 22, measured from aperture 46 to passageway 60.

It is not certain what interaction between the meniscus and the sidewall surfaces creates the phenomenon of meniscus stoppage. Tests have shown that the use of gradually, rather than abruptly, converging sidewall surfaces is preferred, together with edges 62 being limited to a radius of curvature no greater than about 0.02 cm. By this construction, edges 62 act as an energy barrier to capillary flow of liquid and specifically to flow of meniscus 68. The passageway does not, however, block flow of gas since passageway 60 is free of material that would block gas flow.

The convergence of sidewall surfaces 32 and 34 in zone 22 need not be at a constant rate. Alternatively, vessel 20 is useful if sidewall surfaces 32 and 34 converge at an increasing rate as flow proceeds to passageway 60 (phantom lines for zone 22, FIG. 1). In such an alternate embodiment, the sidewall surfaces are concave and provide an increased volume for zone 22.

The stoppage of liquid flow at edges 62 is designed to occur when most, and preferably substantially all of the liquid, is within zone 22. That is, the volume of the liquid is selected to be consistent with the volume of zone 22. Only a negligible amount, if any, shown as portion L, should project out of the reaction vessel, as it is desired in at least immunoassay uses of the vessel that all of the predictable volume of liquid react in zone 22 with a immuno-reagent. For this reason, at least for tests involving constant liquid volumes, at least cover member 42 is preferably substantially rigid, in both zones 22 and 24. As used herein, a "substantially rigid member" is a member having, when freely spanning a distance equal to the width or length of either zone of the element, and with atmospheric pressure on both sides of the member, a free-span deflection, hereinafter "sag," that does not exceed about 0.025 mm. In zone 22, if member 42 has any appreciable sag, one or both of the following could occur: The sagging portion could act as a "meniscus control means," prematurely stopping the meniscus before passageway 60 is reached. Alternatively, the sagging portion could cause air entrapment in the vicinity thereof. In either case, the entire volume of added liquid would not flow into zone 22 and the interaction with the reagent of that zone would not occur to the desired extent.

Cover member 42 is preferably rigid at zone 24 because sagging portions could again form air entrapment. Such air entrapment could prevent transfer of all of the liquid from the first zone to the second zone.

Although it is not critical to an understanding of the invention, it is believed that shape of the meniscus as it approaches the passageway is at least partially responsible for the stoppage of the meniscus. If the meniscus has the shapes shown as 68', angled to the sidewall surfaces as passageway 60 is approached, FIG. 1, it does stop at the passageway, in the absence of applied, externally generated pressures.

Figure 4:
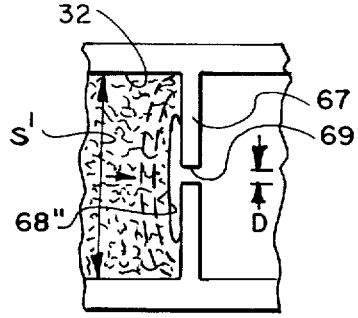
FIG. 4 is a fragmentary plan view of a device similar to that of FIG. 1, but which is a comparative example rather than an embodiment of the invention.

In contrast, FIG. 4, sidewall surfaces modified so as to abruptly alter the spacing s' at the control passageway, e.g., by the use of a wall 67 extending generally perpendicularly from sidewall surface 32, will not stop the capillary liquid flow. (In this example, aperture 69 has spacing D comparable to distance "d" of passageway 60 previously described.) Instead of being stopped, flow of liquid through aperture 69 continues at a retarded rate as is described in U.S. Ser. No. 101,662, now the aforesaid U.S. Pat. No. 4,310,399. The meniscus 68" tends to have a shape that is roughly parallel to wall 67 in this instance, in the vicinity of aperture 69.

Figure 3:
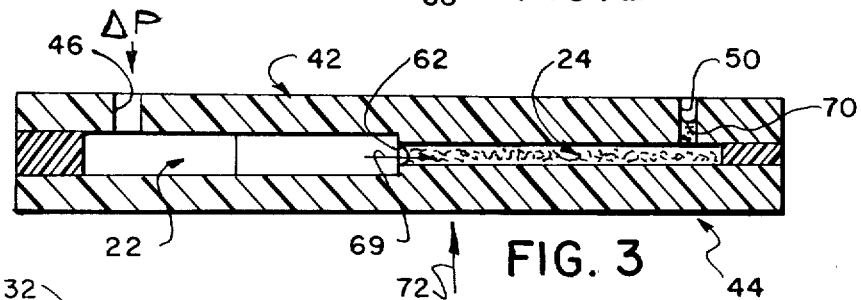
FIG. 3 is a section view similar to that of FIG. 2 but schematically illustrating subsequent steps in its use.

Sidewall surfaces 32 and 34 preferably extend, FIG. 1, from edges 62 into zone 24 with a configuration that aids in the emptying of all the liquid into zone 24, FIG. 3, once flow starts past edges 62. Specifically, the sidewall surfaces preferably diverge into zone 24 from passageway 60 with a constantly increasing spacing $s^2$, FIG. 1, or at an increasing rate (shown in phantom as convexly curved walls).

The pressure $\Delta P$, FIG. 3, needed to push the liquid meniscus past edges 62 is an inverse function of the spacing d and is other than that due to the hydrostatic head of liquid in zone 22. Accordingly, that spacing is selected to provide sufficient stoppage of the meniscus 68 without requiring the use of excessive external pressures. A preferred value of d is about 0.04 cm. If distance h' is about 0.03 cm, the distance from aperture 46 to passageway 60 is about 0.9 cm, and d is about 0.04 cm, the pulse of pressure necessary to push a serum meniscus past the passageway is about 800 dynes/cm². Lesser values of d will require greater pressures to overcome the stoppage of flow at passageway 60.

A further important aspect of this invention is that it is the increased capillary attraction provided by the reduced capillary spacing h' of zone 24, FIG. 2, that provides the completion of the transfer of liquid from zone 22 to zone 24, rather than the displaced air created by the externally generated pressure. The advantage is that such capillary attraction is effective to provide complete transfer, even if the volume of liquid in zone 22 deviates slightly from the expected volume. The use of pressure displacement to displace a given volume of liquid equal to the displaced air volume would not be readily adjustable for such liquid volume deviations. Therefore, the $\Delta P$ pressure applied to push the meniscus into zone 24 is only an impulse the duration of which is by itself insufficient to transfer all the liquid. A duration of between about 1 and about 10 milliseconds is sufficient in many cases to push the meniscus 68 into zone 24, where the increased capillary attraction completes the transfer.

To minimize shear stresses as liquid is forced to flow through passageway 60, the length l of the passageway 60, FIG. 2, is minimized. Specifically, by providing sharp edges 62 with a negligible length in the direction of fluid flow therepast, preferably no greater than about 0.03 cm, the shear stresses that occur when liquid flows through passageway 60 are minimized. Such minimized shear stresses permit the processing of whole blood, as is described hereinafter.

The preferred gas used to form the pulse of pressure $\Delta P$ is air, as is described herein. It will be appreciated that other gases are also useful, most preferably those that are inert relative to the liquid and the reagents used.

Although an immiscible liquid is useful also as a medium for delivering the pulse of pressure, gas is the preferred medium inasmuch as an immiscible liquid could move ahead of the reaction liquid and prevent complete transfer of the desired liquid to the second zone.

The behavior of liquid introduced into zone 22 at aperture 46 will be apparent from the preceding. That is, distance h is such that liquid introduced into zone 22 without any significant external pressure will flow within and through the zone between transport surfaces 26 and 28 by capillary attraction. A characteristic of passageway 60 is that the advancing liquid meniscus 68 stops at edge 62 even in those instances in which minor amounts of liquid L remain above aperture 46, FIG. 2. The liquid remains temporarily stopped at edges 62 while any gas generated in zone 22 is free to flow into zone 24. Thereafter, an externally generated air pressure impulse $\Delta P$, FIG. 3, is applied to the liquid in zone 22. The pressure is applied by any conventional pressurizer, not shown. The energy barrier of edges 62 is overcome by this applied air pressure, and the liquid of zone 22 flows, arrow 69, into zone 24. As noted, the applied pressure is preferably insufficient to cause, itself alone, a completion of the transfer of liquid from zone 22 to zone 24. In accord with well-known principles of capillarity, the smaller spacing of distance h' insures that the liquid will preferentially flow into zone 24 until zone 22 is empty, and further that the liquid will not return to zone 22. Air is pushed out apertures 50 ahead of the advancing meniscus. The meniscus stops (at 70, FIG. 3) when it reaches those apertures. Additional processing then takes place in zone 24, for example, a reaction with additional reagents, or a measurement of analyte in the liquid by an appropriate scan, arrow 72, using electromagnetic radiation that passes through either member 44, as shown, or member 42 if exposed from above (not shown). If the direction of scan is as indicated by arrow 72, member 44 is preferably transparent, at least in the area of zone 24. If zone 22 is scanned also, the entire member 44 is preferably transparent.

Measurements conducted in the second zone are selected to be compatible with the reagent, if any, and the interaction provided in the first zone. Useful examples of measurements include radiometric detection of a radiometrically detectable change. Specifically, a photometer or a fluorimeter is useful to reflectively detect the production of a dye density or to detect a fluorescence, respectively. Also, measurements using the detection of radioactive labels are possible with this vessel.

Specific useful materials for members 42, 44, and spacer member 30 include materials such as cellulose triacetate and materials, such as polypropylene, polystyrene, polyethylene, styrene-butadiene and ABS plastic, that are coated with a surfactant. These materials are sufficiently rigid at the desired thicknesses, for example, from about 0.018 to about 0.04 cm, for cover member 42. In addition, a flexible material such as a 25-micron polyethylene sheet is useful to provide the liquid transport surface of the cover member if it is laminated to a sheet selected from one of the rigid materials noted above.

As an alternative to the use of a reduced value of h', liquid can be preferentially and permanently emptied from zone 22 into zone 24 by the use of a surfactant soluble in the liquid, that is coated on either or both of surfaces 26 and 28. The surfaces in this instance are formed from relatively non-wettable materials such as polystyrene. As used herein, "non-wettable" and "wettable" represent a condition best measured by the contact angle between the liquid and the surface in question. More specifically, a surface is generally considered non-wettable if the contact angle is greater than or equal to 90° and wettable if it is less than 90°. The coating is applied to both zones 22 and 24 (not shown) but only the surfactant of the first zone need be soluble in the liquid. Useful surfactants include, for example, a nonylphenoxy polyglycidol surfactant obtainable under the trade name "Olin 10G" from Olin Corp., Chemicals Div., 120 Long Ridge Rd., Stamford, Conn. As long as the surfactant remains on the surfaces, the liquid will wet the hydrophobic surface and zone 22 can be filled. However, the surfactant immediately dissolves from the walls of zone 22 when wetted. Therefore, after the liquid flows into zone 24, a thin film residue of liquid apparently forms and evaporates, and surfaces 26 and 28 of zone 22 revert back to being essentially non-wettable. Thus, the liquid cannot return to zone 22. In such an embodiment, any distance h' effective to insure capillary flow into zone 24, such as 1 mm or less, is useful regardless of its relationship to distance h of zone 22. That is, the trailing meniscus (not shown) of liquid exiting zone 22 "sees" a surface condition that is essentially non-wettable. In contrast, the advancing meniscus 68 readily wets the surfactant-coated surfaces. The result is an imbalance in driving forces, causing the liquid to empty from zone 22 into zone 24. Furthermore, the hydrophobic nature of the surfaces of now-emptied zone 22 is a sufficient energy barrier to return flow.

The previous embodiments are based on the assumption that once the liquid has moved into the second zone, no significant amount of the liquid should remain in or flow back to the first zone, such as by a return flow through the meniscus control passageway. However, in some instances it is permissible and desirable for liquid to remain in or return to the first zone, for example if the first zone of the reaction vessel is to be used to carry out an additional reaction on reaction products produced in the second zone. For this embodiment, distances h and h' between the opposed transport surfaces of the two zones are preferably equal (not shown) and preferably no water-soluble surfactant is used. An impulse of pressure, if of short duration as for the previous embodiments, will only move the liquid part-way into the second zone where it can react with a reagent in that zone. An additional reagent is immobilized in the first zone, selected to react only with the reaction products produced by the reagent of the second zone. As each reaction takes place in its respective zone, a concentration gradient is created that induces diffusion of the necessary ingredient or reaction product to the zone where that reaction takes place.

Figure 5:
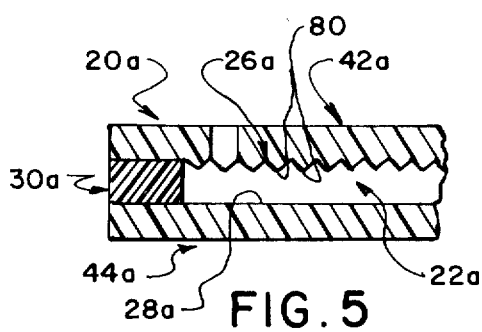
FIGS. 5 through 7 are fragmentary section views similar to that of FIG. 3, but illustrating alternate embodiments of the invention.

Either of the opposed surfaces 26 and 28 can be nominally smooth, as shown in the embodiment of FIG. 2, or they can be provided with a regular pattern of grooves, FIG. 5. Parts similar to those previously described bear the same reference numeral, to which the distinguishing suffix "a" has been attached. Thus, vessel 20a comprises a cover member 42a, support member 44a, and spacer member 30a defining a first zone 22a, a second zone not shown, and a meniscus control means as described above. Undersurface 26a, however, is provided with grooves spaced apart a regular distance by sawtooth ridges 80. Preferably the ridges are mutually parallel and extend perpendicularly to the bisector line between the sidewalls. If surface 28a is optionally grooved, not shown, the grooves preferably extend at a positive angle to the grooves and ridges 80 of surface 26a in the manner taught by U.S. Pat. No. 4,233,029, issued Nov. 11, 1980. The details of that patent are expressly incorporated herein by reference.

Figure 6:
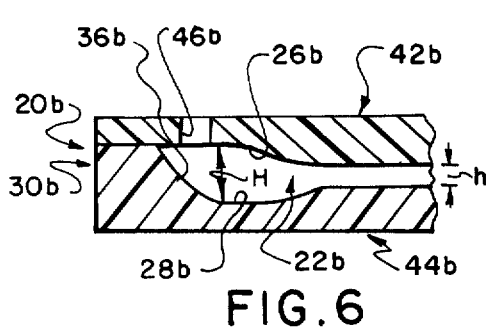

It is not essential that the spacing of surfaces 26 and 28 be capillary precisely at the location of aperture 46, as is demonstrated in the embodiment of FIG. 6. Parts similar to those previously described bear the same reference numeral to which the distinguishing suffix "b" is applied. The vessel 20b comprises member 42b and 44b, member 42b having an inlet aperture 46b permitting liquid introduction into zone 22b. However, unlike previous embodiments, spacing H at the aperture 46b is optionally non-capillary, surfaces 26b and 28b being shaped to gradually converge to a capillary spacing h at the portion of zone 22b contiguous with the meniscus control passageway (not shown). No sharp edges are present to create a barrier to flow. This embodiment uses injection metering of sufficient pressure to move liquid into that portion of zone 22b wherein the spacing is distance h and capillary action takes over to maintain flow towards the meniscus control passageway. The injection pressure is selected such that the pressure behind the meniscus when it reaches the meniscus control passageway, is significantly less than the $\Delta P$ pressure necessary to overcome the energy barrier of that passageway. End wall 36b is preferably sloped in this embodiment, to deflect incoming liquid to insure that the liquid continues, under the injection pressure, to advance to the point where capillary flow begins.

This embodiment also demonstrates that the spacer member, here shoulder 30b, can be an integral part of member 44b, as shown, or of member 42b.

Figure 7:
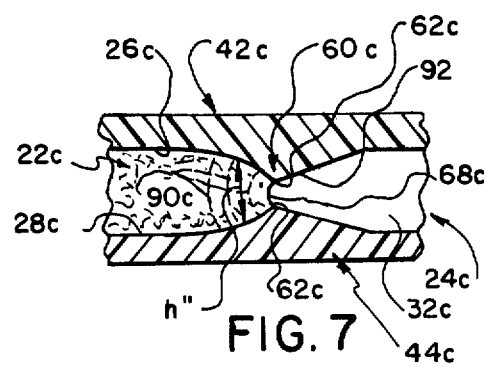

The meniscus control means between the two zones need not be defined by the sidewall surfaces. In the embodiment of FIG. 7, it is provided by the spaced-apart transport surfaces of the zones. Parts similar to those previously described bear the same reference numeral to which the distinguishing suffix "c" is applied. Thus, vessel 20c comprises a cover member 42c and support member 44c that provide opposed transport surfaces 26c and 28c, preferably formed from hydrophobic materials coated with a water-soluble surfactant as described above. Zones 22c and 24c are provided, separated by a meniscus control means in the form of a narrowed passageway 60c, as described in the previous embodiment. However, in this embodiment, the sharply defined edges 62c of the passageway 60c comprise opposed ridges in the opposed transport surfaces 26c and 28c that extend from sidewall surface 32c to the opposite sidewall surface. The shape of the opposed transport surfaces preferably is such that the advancing meniscus, as it approaches passageway 62c, extends generally perpendicularly, dashed lines 90, to the surfaces forming edges 62c. This meniscus shape apparently ensures that the edges 62c act as an energy barrier to further meniscus flow. Most preferably, those surfaces are shaped so that distance "h'''" between these surfaces is reduced at an increasing rate in the vicinity of passageway 60c to create opposed concavities immediately adjacent the edges 62c. As in previous embodiments, the length of passageway 60c in the direction of flow preferably does not exceed about 0.03 cm.

It will be appreciated that, because the meniscus control means comprise features of opposed transport surfaces 26c and 28c, the spacing between the sidewall surfaces is of no consequence to the stoppage of the meniscus. Such spacing can be selected to be constant or variable, as desired.

Preferably, zone 24c features opposed surfaces 92, here portions of surfaces 26c and 28c, that extend into that zone from passageway 60c at a separation distance that increases at a constant or at an increasing rate. Such a rate of separation helps to insure that once the liquid meniscus moves into zone 24b, all the liquid flows into zone 24b.

Figure 8:
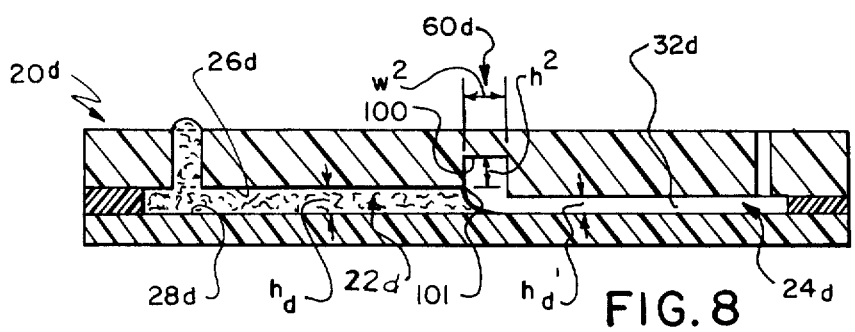
FIGS. 8 and 9 are section views similar to that of FIG. 3, but illustrating still other additional embodiments.
Figure 9:
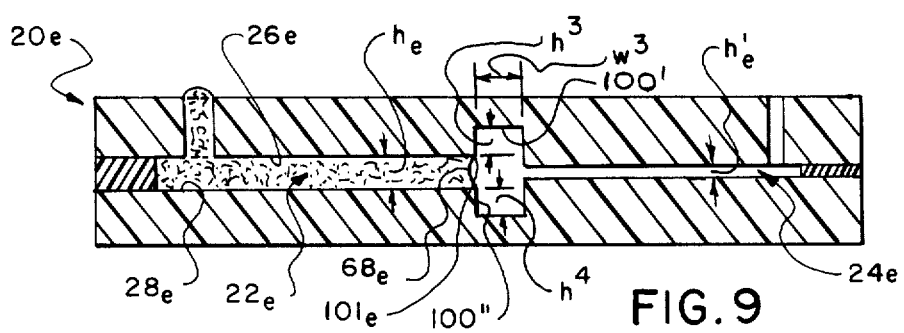

In the embodiments of FIGS. 8 and 9, the meniscus control means features a sudden increase in the capillary spacing between the opposed transport surfaces, rather than a narrowing of the spacing. Parts similar to those previously described bear the same reference numeral to which the distinguishing suffixes "d" and "e," respectively, are appended.

Thus, vessels 20d and 20e are constructed in the same manner as the vessel of FIG. 1, with opposed transport surfaces 26d and 28d, or 26e and 28e, respectively. These surfaces together with sidewall surfaces such as surface 32d form first and second zones 22d and 24d, or 22e and 24e, respectively, separated by the meniscus control means. However, in the embodiment of FIG. 8, the meniscus control means 60d comprises a channel 100 in at least one of the opposed surfaces, here surface 26d, having a depth $h^2$ and a width $w^2$ that are sufficient to create an energy barrier to meniscus flow, and thus to stop flow. Specifically, the energy barrier comprises the sharp edge 101 created in surface 26d by the sudden depth $h^2$ of channel 100. The channel extends the full width between the zones, in order to be effective. Most preferably, the sharp edge of the energy barrier is created by a channel having a depth $h^2$ that is at least about 0.02 mm greater than the spacing $h_d$ between surfaces 26d and 28d, and a width $w^2$ that is greater than or equal to $h_d$. As in the embodiment of FIG. 1, distance $h_d'$ of zone 24d is significantly less than distance $h_d$ of zone 22d, and the total volumes of the two zones are adjusted to be generally equal. The radius of curvature of edge 101 preferably does not exceed about 0.02 cm.

In the embodiment of FIG. 9, the meniscus control means comprises a pair of opposed channels 100' and 100", each with a depth $h^3$ and $h^4$, respectively, and a width $w^3$. To create the energy barrier to capillary flow, both edges 101e and 101e' are sharp as before and the combined depth $(h^3+h^4)$ is preferably at least about 0.015 mm greater than the distance $h_e$. Width $w^3$ need not have the same relationship to $h_e$ as $w^2$ has to $h_d$ in the embodiment of FIG. 8. Preferably $w^3$ is at least 25 microns. Distance $h_e'$ is at least 25% less than $h_e$.

A total depth $(h_e+h^3+h^4)$ that is greater than a capillary spacing is also useful. The externally generated pressure is selected to be large enough to move meniscus 68e into contact with zone 24e. A pressure of at least 800 dynes/cm$^2$ is useful for channels 100' and 100" having depths such that $h^3+h^4+h_e$ total about 0.415 mm, and a common width $w^3$ equaling 25 microns.

The aforedescribed reaction vessels are particularly useful to provide a variety of interactions in a first zone containing an interactive reagent, between the reagent and material of the liquid, followed by analysis in the second zone. As used herein, a "reagent" means any substance that is interactive with a material, such as an analyte, of the liquid, or a decomposition or reaction product of that material. "Interaction" and "interactive" refer to chemical reactions, catalytic activity such as enzymatic reactions, immunological reactions, or any other form of chemical or physical interaction that can result in the production of a useful result in the second zone. Preferred are those interactions that permit analysis of the material of the liquid. Highly preferred are binding reactions in which a reagent immobilized in the first zone binds to at least a portion of the material of the liquid, thus retaining that bound portion in the first zone. This binding reaction occurs whether the materials to be bound are labeled or unlabeled. If the vessel is to be used as an immunoassay device, as described hereinafter, both labeled analog and unlabeled analyte comprise the material that binds, in a competing fashion, to the reagent. If the vessel is to be used as a test device for whole blood, also as described hereafter, the materials that bind are the cells of whole blood, which need not be labeled for purposes of the test.

Preferably the reagent is immobilized on one or both of the sidewall surfaces or the opposed capillary transport surfaces of the first zone of the vessel of the invention. Alternatively, and particularly in those instances in which a relatively high volume of material is to interact with the immobilized reagent, the reagent is immobilized on fillers such as beads as described in European patent application No. 13,156, published July 9, 1980. The beads in turn are disposed in the first zone and secured in place, for example by the use of a water-insoluble adhesive of the type described in the aforesaid European patent application No. 13,156. In yet another embodiment (not shown) the beads are loosely disposed in the first zone, having a size that prevents them from passing through passageway 60. In this embodiment, distance "d" is substantially less than distance "h."

As used herein, "immobilized" refers to a condition of immovable adherence created by any mechanism, such as chemical bonding, that is sufficient to withstand the pressures and stresses generated within the zones during use of the vessel or test device. A reagent is immobilized to one of the surfaces of the transport zone, or to inert fillers in the zone, if that reagent is bonded or adsorbed directly thereto, or if it is bonded via an intermediate, water-insoluble material that is itself secured to the zone.

Highly preferred reagents include those which produce immuno-reactions, such as antibodies or antigens, herinafter "immunogens." The material of the liquid in such a case is the corresponding immunogen, that is, the antigen or antibody, respectively. Any immuno-reaction is detectable using the vessel of the invention, by the procedure hereinafter described. Immunological reagents, hereinafter "immunogen reagents," are preferably immobilized by being adsorbed or covalently bonded by any conventional procedure to any of the surfaces of the first zone, or to beads that are secured to the first zone. One example of a useful procedure for covalently bonding an immunogen reagent is as follows:

A polyacrylamide is selected to which the immunogen reagent is to be secured. This is either the material of the walls of the zone, or polyacrylamide beads adhered to the walls by a water-insoluble adhesive. The polyacrylamide in turn is partially hydrolyzed or hydrazinolyzed to permit covalent bonding by the antibodies. Details are described, for example, in U.S. Pat. No. 3,853,987.

Indirect covalent bonding is also useful, wherein a coupling agent is used having groups that will covalently bond with both the immunogen reagent and the walls of the zone (or beads secured to the zone). For example, covalent bonding of an immunogen reagent to ceramic beads is possible using the intermediate coupling agents described in U.S. Pat. No. 3,652,761.

Figure 10:
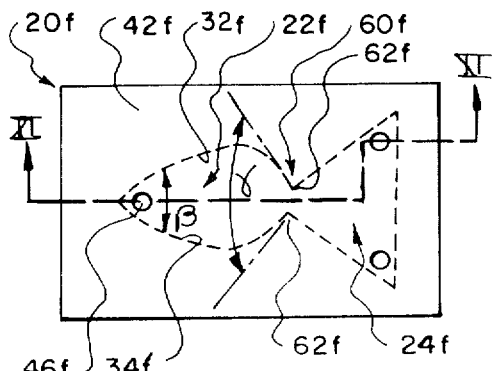
FIG. 10 is a plan view similar to that of FIG. 1, illustrating an embodiment particularly adapted for the detection or measurement of antibodies or antigens.
Figure 11:
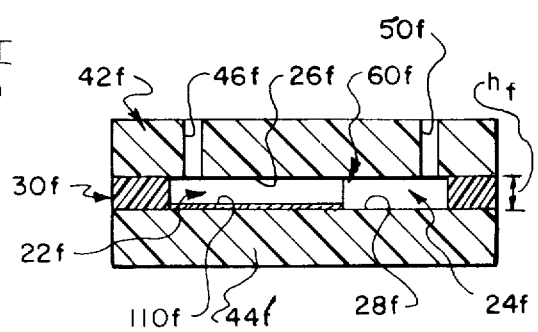
FIG. 11 is a section view taken generally along the line XI—XI of FIG. 10.
Figure 12:
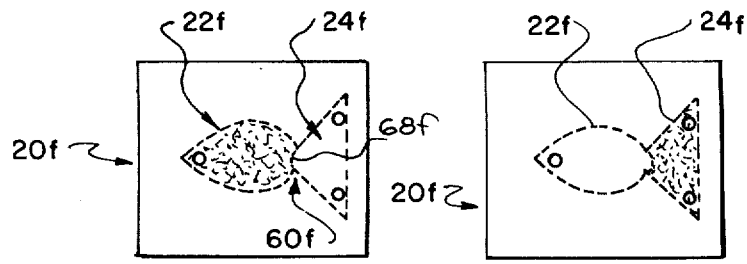
FIGS. 12a and 12b are plan views demonstrating the use of the device of FIG. 10.

The selection of an immunogen as the reagent permits immunoassays to be conducted using the vessel of the invention. The embodiment of FIGS. 10–12 is illustrative of a vessel adapted to such a use. Parts similar to those previously described bear the same reference numeral to which the distinguishing suffix "f" is applied. Thus, vessel 20f is a test device comprising first and second zones 22f and 24f, formed by cover member 42*f* and support member 44*f*, separated by spacer member 30*f*, FIG. 11. The two zones are separated but fluidly connected by narrowed passageway 60*f* as the meniscus control means. As shown, passageway 60*f* features two opposed edges 62*f* in sidewall surfaces 32*f* and 34*f*. Aperture 46*f* in member 42*f* permits liquid introduction and apertures 50*f* permit air venting. In this embodiment, to minimize air entrapment, sidewall surfaces 32*f* and 34*f* are joined to form an angle beta ($\beta$) where end wall 36 would otherwise be, and aperture 46*f* is on the bisector of angle $\beta$, FIG. 10. Angle $\beta$ is preferably between about 7° and 75°, and most preferably, 60°. Wall surfaces 32*f* and 34*f* curvilinearly connect with passageway 60*f* to prevent the advancing wavefront from encountering edge discontinuities before encountering edges 62*f*. As passageway 60*f* is neared, surfaces 32*f* and 34*f* converge at an increasing rate, consistent with the absence of edge discontinuities other than edge 62*f*. If angle $\beta$ is about 60°, then the angle of convergence $\gamma$, FIG. 10, is preferably about 120°.

Most preferably, an immunogen reagent for a particular complementary immunogen is immobilized in the first zone, in the form, for example, of a coating 110*f* bonded to surface 28*f* of zone 22*f*, FIG. 11. Preferably, surface 26*f* bears a water-soluble surfactant (not shown) as discussed for previous embodiments. A known amount of the analog having an appropriate label is added to zone 22*f* either as an additional pre-applied reagent or as a liquid added with, to, or after the unknown sample. It will be appreciated that care is taken not to admix the analog and the immunogen reagent before adding the immunogen of the liquid to be assayed. The label is any detectable species, for example, an enzyme, a fluorescent species, or a radioactive species, chemically or physically linked (such as by adsorption) to the antigen or antibody. For example, a fluorescent species such as fluorescein is covalently bonded to an antigen. In a preferred embodiment, a polymeric latex bead is "loaded" with a fluorescent rare earth chelate, preferably a europium or terbium chelate. The resultant rare earth chelate-loaded latex bead is employed as a fluorescent label to which the analog of choice is physically adsorbed or covalently bonded. These latex polymer beads preferably have an average diameter of from about 0.01 to about 0.2 micron and are "loaded" with up to about 7.5 weight percent of the rare earth chelate. Because of the large number of rare earth chelate molecules which can be loaded into a single latex bead, the resultant label is highly fluorescent and provides immuno-fluorescence exhibiting excellent sensitivity. A highly preferred analog is one employing a fluorescent, rare earth chelate-loaded polymeric latex bead as described in Frank and Sundberg, European patent application No. 002,963, published Nov. 7, 1979, and incorporated herein by reference. While the liquid and meniscus 68*f* are retained in the first zone by the meniscus control means, FIG. 12*a*, the analog and the immunogen to be assayed complete for binding to the immunogen reagent which is immobilized in the first zone 22*f* of the vessel. After an appropriate length of time, for example, 5 to 15 minutes, a pulse of pressure such as 800 dynes/cm$^2$ is applied to force the liquid to empty from the first zone into the second, FIG. 12*b*, carrying immunogen and analog that have not become bound to the immunogen reagent.

Useful methods of measurement to determine the concentration of immunogen which are then employed include: (A) detecting the unbound analog which has flowed into the second zone, and/or (B) detecting the analog which remains bound to the immobilized immunogen reagent in the first zone. In either method, the amount of immunogen in the liquid sample is determined based on the detected concentration of analog in accordance with conventional immunological techniques. Such techniques are set forth in European patent application No. 13,156, published July 9, 1980, the details of which are hereby expressly incorporated by reference.

It has been determined that the ionic bond formed in an immuno-reaction is sufficient to withstand the shear force generated by the pulse of pressure used to force plasma, for example, having a viscosity of 2.4 centipoise, to flow from zone 22*f* into zone 24*f* past passageway 60*f*. That is, under less than the best conditions, the shear force likely to occur can be shown to be about $2 \times 10^{-4}$ nt/molecule. The energy bond strength can be shown to be about $10^{-10}$ nt/molecule, more than enough to resist the stress.

An advantage of vessel 22*f* is that the concentration determined by the measurement made in zone 24*f* of free analog, can be checked by measuring the bound analog in zone 22*f*.

The vessel of the invention containing the immobilized form of the reagent in the first zone has other uses in addition to immunological assays. Such immobilized reagents permit the vessel of the invention to be used as a test device for whole blood. In such an embodiment, the immobilized reagent is selected to be a red cell-agglutinating reagent. Such a reagent attracts or binds substantially all the red blood cells of whole blood added to the device, leaving only the plasma and its contained analyte material free to flow into the second zone when an externally generated pulse of pressure is delivered to the liquid of the first zone in the manner described above. The necessary reagents for analyzing the analyte material of the plasma are contained in the second zone.

Useful examples of such reagents for immobilizing the red cells include agglutinating reagents such as positively charged polymers, e.g., polybrene; lectins; high molecular weight dextrans; and phytohemagglutinin as described in U.S. Pat. No. 3,146,163, and U.S. Pat. No. 3,902,964. The last-noted materials are proteinaceous, and as such are subject to bonding to appropriate surfaces, such as polyacrylamide, by the procedures described above. Thus, agglutinating agents are readily immobilized to the wall surfaces of the first zone and/or to beads secured to the first zone.

Figure 13:
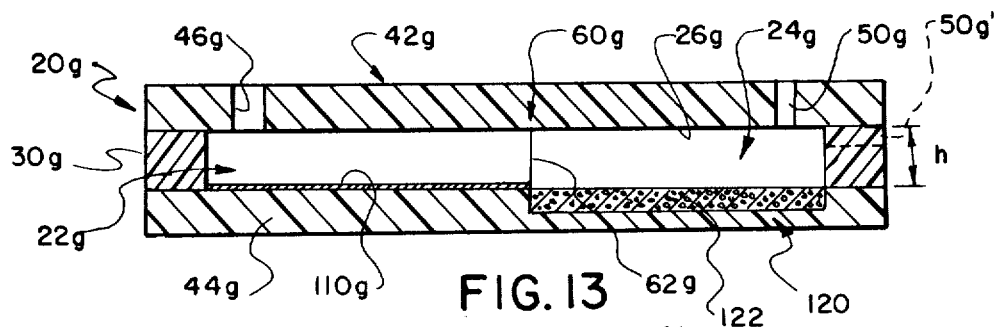
FIG. 13 is a section view similar to that of FIG. 2 or 3, illustrating an embodiment particularly adapted for detection of an analyte of whole blood.

The embodiment of FIG. 13 illustrates a vessel constructed in the above manner as a test device for the measurement of an analyte of whole blood. Parts similar to those previously described bear the same reference numeral to which the distinguishing suffix "g" is applied. Thus, vessel 20*g* comprises opposed members 42*g* and 44*g* and specer member 30*g*, forming first and second zones 22*g* and 24*g* with a meniscus control means in the form of a narrowed passageway 60*g* between them, as before. Apertures 46*g* and 50*g* are formed as before for introduction of liquid and for air venting. Also as in the case of the device of FIG. 11, a reagent coating 110*g* is applied to at least one of the walls of zone 22*g* directly, or to beads adhered within the zone, not shown. Surface 26*g* of both zones 22*g* and 26*g* preferably bears a water-soluble wetting agent or surfactant (not shown), and the material of members 42*g*, 44*g*, and 30*g* is selected to be relatively non-wetting. The beads, if used, preferably occupy less than 50% of the volume of zone 22g. In this case, the reagent is an agglutinating agent such as phytohemagglutinin, immobilized as described above.

Alternatively, the vent apertures may be formed in spacer member 30g, as shown by the dashed lines 50g' of FIG. 13. Preferably, such apertures are formed by notching the top of spacer member 30g.

To permit the analysis of the now-separated plasma as it enters zone 24g in response to the externally generated pressure, an analyte detection element 120 is provided in or adjacent to member 44g in zone 24g, spaced from surface 26g. Preferably the detection element comprises one or more detection reagent layers 122 having a variety of binder compositions and a variety of detection reagents. For example, gelatin, cellulose acetate, polyvinyl alcohol, agarose and the like are useful binders, the degree of hydrophilicity of the layer being dependent upon the material selected.

Additional layers disposed above layer 122 are useful to provide a variety of chemistries or functions. If used, these additional layers provide additional detection reagents, or filtering, registration and/or mordanting functions, such as are described in U.S. Pat. No. 4,042,335, issued on Aug. 16, 1977.

As used herein, "detection reagent" means a material that is capable of interaction with an analyte, a precursor of an analyte, a decomposition product of an analyte, or an intermediate of an analyte, to ultimately produce a detectable response. Useful detection elements in many instances include a first detection reagent that produces from the analyte an intermediate or a decomposition product, and a second detection reagent, labeled "indicator" because of its function, that is responsive to the intermediate or decomposition product to produce said change. Useful detection reagents also include preformed, radiometrically detectable species that are caused by the analyte of choice to move out of a radiometrically opaque portion or layer of the detection element, into a radiometrically transparent portion or layer, such as a registration layer which can be layer 122 in contact with member 44g.

The noted interaction between a detection reagent and the analyte therefore includes chemical reactions, catalytic activity as in the formation of an enzyme-substrate complex, or any other form of chemical or physical interaction, including physical displacement, that can produce ultimately a detectable response in the test element. The assay method is designed to produce a response signal that is predictably related to the amount of analyte that is present.

The preferred detection element is designed to measure radiometric responses, produced by impinging electromagnetic energy on the element. As is well known, radiometric detection includes both colorimetric and fluorimetric detection, depending upon the detection reagents selected as the indicator.

The detection element 120 is adaptive to a variety of different analytes. Preferably, the assays are all oxygen-independent, as the flow of liquid into the zone 24g tends to seal off detection element 120 from any additional oxygen. Typical analytes which can be tested include total protein, bilirubin and the like. Useful detection reagents and binder or vehicle compositions for, e.g., layer 122 and any additional layers of the element include those described in, respectively, for those analytes, U.S. Pat. Nos. 4,132,528, issued on Jan. 2, 1979; and 4,069,016 or 4,069,017, issued on Jan. 17, 1978.

Detection element 120 is also useful to test for other analytes.

The method of using vessel 20g will be apparent from the preceding discussion. A quantity of whole blood, for example, a drop, is added to zone 22g via aperture 46g, and the meniscus flows up to edges 62g of passageway 60g, where it stops. Coating 110g comprising a red cell-agglutinating reagent immobilizes the red cells while the liquid remains in zone 22g. After an appropriate length of time, such as 10 minutes, the plasma is separable from the cells by applying an impulse of pressure, such as a pressure of about 800 dynes/cm$^2$, to aperture 46g. The plasma flows into zone 24g and into detection element 120. After an incubation period of up to about five to ten minutes, a radiometric signal is generated which is detected in element 120 by a suitably calibrated radiometer.

Figure 14:
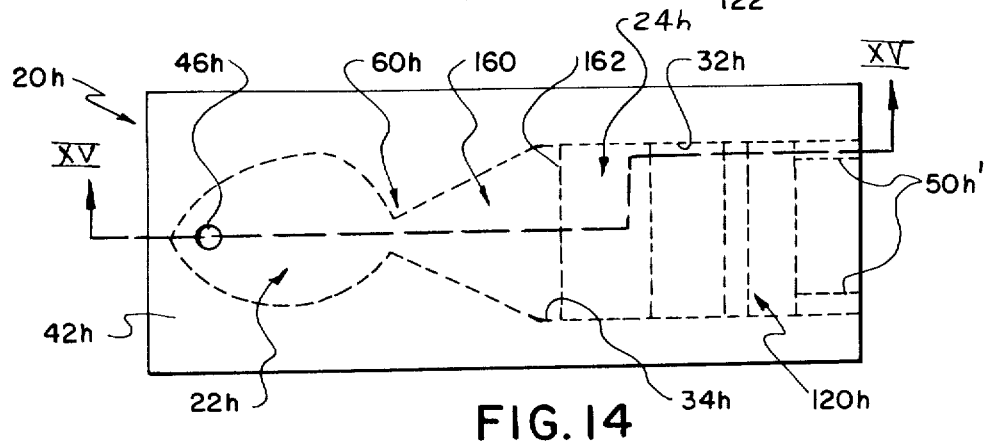
FIG. 14 is a plan view similar to that of FIG. 12a, but illustrating a three-zone embodiment.

More than two zones are useful in the vessel of the invention, meniscus control means preferably being disposed between each pair of adjacent zones. Parts similar to those previously described bear the same reference numeral, to which the distinguishing suffix "h" is added. Thus, FIGS. 14 and 15, vessel 20h comprises opposed members 42h and 44h, spaced apart by spacer member 30h. Aperture 46h permits access of liquid to a first zone 22h having a coating 110h on surface 28h, FIG. 15. Coating 110h comprises a cell-agglutinating reagent bonded to surface 28h, as described for the previous embodiment. Surface 26h is preferably coated with a water-soluble surfactant and members 42h, 44h and 30h are relatively non-wetting, as before. Passageway 60h comprising opposed, sharply-defined sidewall edges 62h, FIG. 15, confines the whole blood within zone 22h to allow the red blood cells to become bound.

Figure 15:
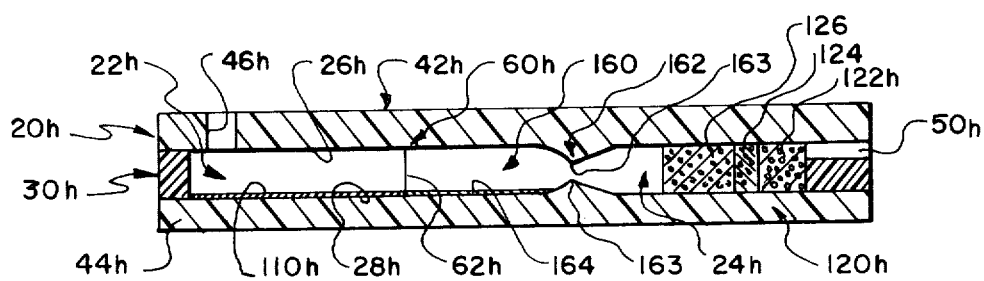
FIG. 15 is a section view taken generally along the line XV—XV of FIG. 14.

Unlike the previous embodiments, vessel 20h has three zones, FIG. 15, of approximately equal volume, two of the additional zones being intermediate zone 160 and analysis zone 24h disposed downstream from zone 22h. Each of the zones is separated from but fluidly connected to the upstream zone by a meniscus control means. Such control means comprise passageway 60h for zone 160 and passageway 162 for zone 24h. Preferably, passageway 162 features opposed edges 163 extending from transport surfaces 26h and 28h, FIG. 15. This arrangement avoids the necessity of gradually increasing the spacing of the spacer member sidewall surfaces 32h and 34h, FIG. 14, that confine the detection element 120h. Zone 160 preferably includes a coating 164, such as on surface 28h, FIG. 15, of a detection reagent additional to those present in detection element 120h located in zone 24h. As shown, detection element 120h is a multi-layered element the layers of which are stacked against the flow of liquid into zone 24h. In a preferred form, detection element 120h comprises at least layer 122h, and optionally, a detection reagent layer 126 and a barrier composition layer 124. The barrier composition is uniformly permeable to a gas such as NH$_3$, but is substantially impermeable, over the time of the test, to interferents such as are carried by water. Because of this arrangement, vent apertures 50h preferably are located in spacer member 30h.

A preferred use of vessel 20h is as a test device for plasma ammonia alone, or for plasma ammonia followed by plasma creatinine. Coating 164 for these uses comprises a buffer selected to maintain a pH of about 9.0 in the plasma, to release dissolved ammonia. A preferred buffer is a mixture of "tris" buffer, comprising tris(hydroxymethylaminomethane), and $KH_2PO_4$. Indicator layer 122h of element 120h comprises an indicator responsive to ammonia that changes color in proportion to the amount of $NH_3$ gas that flows into layer 122h from zone 160 while the plasma is being retained in zone 160. For example, bromophenol blue is useful as the indicator.

Alternatively, element 120h further includes a detection reagent, preferably in layer 126, that decomposes creatinine into $NH_3$ gas, and the described barrier composition, preferably in layer 124, that allows the $NH_3$ but not the liquid of the plasma to permeate. Useful compositions for layers 124 and 126, as well as layer 122h, are described in commonly-owned U.S. Ser. No. 091,218, filed on Nov. 5, 1979, by Goodhue et al and entitled "Creatinine Iminohydrolase Free From Urease Activity," now U.S. Pat. No. 4,276,377, issued June 20, 1981, the contents of which are expressly incorporated herein by reference.

The immediately described alternative construction of vessel 20h and detection element 120h is used first to test for plasma ammonia, and then optionally to test for plasma creatinine. After the plasma is forced into zone 160, coating 164 serves to release plasma ammonia as $NH_3$ gas, which gas flows into zone 24h while the plasma is stopped at passageway 162. The $NH_3$ permeates indicator layer 122h of detection element 120h to interact to produce a detectable color change. After the color change that is proportional to the plasma ammonia is detected, the plasma is analyzed for creatinine content. For this, a second impulse of air pressure is applied at aperture 46h, this time to push the liquid meniscus past passageway 162. The liquid then flows into zone 24h and into detection element 120h. The additional $NH_3$ generated from the decomposition of creatinine is detectable by the same indicator used for the ammonia.

To use vessel 40h as a test device only for plasma ammonia, the second impulse of pressure is simply omitted.

Yet another alternative embodiment of the invention, not shown, comprises the device of FIG. 15 wherein zone 22h is omitted and a previously obtained plasma is placed via an inlet aperture, such as aperture 46h, directly into zone 160. The procedure for the sequential detection of plasma ammonia and/or creatinine is followed as described above.

The invention has been described in detail with particular reference to preferred embodiments thereof, but it will be understood that variations and modifications can be effected within the spirit and scope of the invention.

What is claimed is:

1. In a reaction vessel comprising
   a first zone,
   a second zone adapted to receive liquid flow from the first zone, at least one of said zones containing a reagent capable of interacting with a material of a liquid introduced into said one zone,
   said zones comprising a first member, a cover member, and means for disposing said first member and said cover member in superposed relationship,
   inlet means permitting the introduction of the liquid into said first zone,
   and means providing a passageway fluidly connecting said zones;
   the improvement wherein said first and said cover members provide opposed surfaces spaced apart a distance effective to induce capillary flow of said introduced liquid at least in the portion of said first zone contiguous to said passageway means, and in said second zone,
   and wherein said passageway means includes meniscus control means for stopping the liquid meniscus from proceeding by capillary attraction into said second zone from said first zone, said control means being configured to permit the liquid to flow into said second zone only when an externally generated pressure is applied to the liquid in an amount sufficient to push the liquid meniscus into said second zone.

2. In a reaction vessel comprising
   a first zone,
   a second zone adapted to receive the liquid from the first zone, at least one of said zones containing a reagent capable of interacting with a material of a liquid introduced into said one zone,
   said zones comprising a first member, a cover member, and means for disposing said first member and said cover member in superposed relationship,
   inlet means permitting the introduction of the liquid into said first zone,
   and means providing a passageway fluidly connecting said zones;
   the improvement wherein said first and said cover members provide opposed surfaces spaced apart a distance effective to induce capillary flow of said introduced liquid at least in the portion of said first zone contiguous to said passageway means, and in said second zone,
   and wherein said passageway means includes meniscus control means for stopping the liquid meniscus from proceeding by capillary attraction into said second zone from said first zone, said control means being configured to permit the liquid to pass into said second zone only when an externally generated pressure is applied to the liquid in an amount sufficient to push the liquid meniscus into said second zone,
   said distance of said second zone being less than said distance of said first zone by an amount effective to preferentially attract said liquid, in response to said push of the liquid by the pressure, into said second zone from said first zone and to confine the attracted liquid within the second zone.

3. In a reaction vessel comprising
   a first zone,
   a second zone adapted to receive the liquid from the first zone, at least one of said zones containing a reagent capable of interacting with a material of a liquid introduced into said one zone,
   said zones comprising a first member, a cover member, and means for disposing said first member and said cover member in superposed relationship,
   inlet means permitting the introduction of the liquid into said first zone,
   and means providing a passageway fluidly connecting said zones;
   the improvement wherein said first and said cover members provide opposed surfaces spaced apart a distance effective to induce capillary flow of said introduced liquid at least in the portion of said first zone contiguous to said passageway means, and in said second zone,
   at least one of said two surfaces comprising, in both of said zones, a relatively non-wettable material coated with a surfactant soluble in the liquid and capable of making said surfaces wettable by the liquid, and wherein said passageway means includes meniscus control means for stopping the liquid meniscus from proceeding by capillary attraction into said second zone from said first zone, said control means being configured to permit the liquid to pass into said second zone only when an externally generated pressure is applied to the liquid in an amount sufficient to push the liquid meniscus into said second zone.

4. A vessel as defined in claim 1, 2 or 3, and further including sidewall surfaces cooperating with said two surfaces to define said zones, said sidewall surfaces forming in said passageway means an energy barrier to meniscus flow such that the liquid meniscus stops at said barrier.

5. A vessel as defined in claim 4, wherein said sidewall surfaces in said second zone adjacent to said passageway means diverge from said meniscus control means into said second zone at a constant or at an increasing rate.

6. A vessel as defined in claim 5, wherein the rate of divergence between said sidewall surfaces of said second zone increases with distance from said meniscus control means.

7. A vessel as defined in claim 1, 2, or 3, wherein said meniscus control means comprises a pair of opposed ridges in said two opposed surfaces that provide a reduction in said spaced-apart distance.

8. A vessel as defined in claim 7, wherein said distance reduction between said two opposed surfaces increases in rate as said meniscus control means is approached from said inlet means.

9. A vessel as defined in claim 1, 2, or 3, wherein said meniscus control means comprises a channel in at least one of said two opposed surfaces having a depth and width sufficient to stop the meniscus from flowing into said second zone.

10. A vessel as defined in claim 9, wherein said channel depth is at least about 0.02 mm greater than said spaced-apart distance between said two opposed surfaces.

11. A vessel as defined in claim 9, wherein said meniscus control means comprises two opposed channels, one in each of said opposed surfaces, having a combined depth that is at least 0.015 mm greater than said spaced-apart distance between said two opposed surfaces.

12. A vessel as defined in claim 1, 2 or 3, wherein at least said cover member is substantially rigid.

13. A vessel as defined in claim 1, 2, or 3, wherein said distance is effective to induce capillary flow of said introduced liquid from said inlet means to said passageway means.

14. A vessel as defined in claim 1, 2, or 3, and further including sidewall surfaces cooperating with said two surfaces to define said transport zones, said sidewall surfaces and said two surfaces forming said passageway means with a length in the direction of liquid flow therethrough that is no greater than about 0.03 cm.

15. A vessel as defined in claim 4, wherein said energy barrier comprises opposed edges in said sidewall surfaces.

16. A test device comprising two opposed transport surfaces and means for spacing them apart a distance to define at least two fluidly connected zones connected by a passageway, said distance being effective to induce capillary flow of introduced liquid in said zones, one of said zones containing inlet means permitting the introduction of a liquid into said one zone, and a reagent immobilized in said one zone, said reagent being capable of binding with a material of the liquid and with a known, labeled amount of said material;

the other of said zones being adapted to receive by said passageway liquid from said one zone and material contained in the liquid that is not bound to said reagent;

and meniscus control means associated with said passageway for stopping a liquid meniscus from proceeding into said other zone from said one zone, said control means being configured to permit the liquid and unbound material to pass into said other zone only when an externally generated pressure is applied to the liquid in an amount sufficient to push said meniscus into said other zone.

17. A device as defined in claim 16, wherein said meniscus control means comprises a pair of opposed ridges in said two surfaces that provide a reduction in said spaced-apart distance.

18. A device as defined in claim 16, wherein said meniscus control means comprises a channel in at least one of said two surfaces having a depth and width sufficient to stop the meniscus from flowing into said other zone.

19. A device as defined in claim 16, wherein at least one of said two surfaces comprises, in both of said zones, a relatively non-wettable material coated with a surfactant soluble in the liquid and capable of making said surfaces wettable by the liquid.

20. A device as defined in claim 16, wherein said means for spacing includes sidewall surfaces cooperating with said two surfaces to define said transport zones connected by said passageway, said sidewall surfaces and said two surfaces forming said passageway with a length in the direction of liquid flow therethrough no greater than about 0.03 cm.

21. A device as defined in claim 16, wherein said material is an immunogen present in a biological liquid, said reagent is the immunogen complement, and said other of said zones is adapted for detection of labeled material.

22. A device as defined in claim 21, wherein both of said zones are adapted for detection of said labeled material.

23. A device as defined in claim 16, wherein said means for spacing includes sidewall surfaces cooperating with said two surfaces to define said zones connected by said passageway, said sidewall surfaces forming in said passageway an energy barrier to meniscus flow such that the meniscus of the liquid stops at said meniscus control means.

24. A device as defined in claim 23, wherein said meniscus control means comprises opposed edges in said sidewall surfaces.

25. A device as defined in claim 16, wherein said spaced-apart distance is effective to induce capillary flow of said introduced liquid at least in the portion of said one zone contiguous to said passageway, and in said other zone.

26. A device as defined in claim 25, wherein said spaced-apart distance of said other zone is less than said spaced-apart distance of said one zone by an amount effective to preferentially attract said liquid in response to said push of the liquid by the pressure into said other zone from said one zone, and to confine the attracted liquid within said other zone.

27. A test device for the measurement of an analyte of whole blood, comprising
   two opposed transport surfaces and means for spacing them apart a distance to define at least two fluidly connected zones and a passageway connecting them, said distance being effective to induce capillary flow of introduced liquid in said downstream zone and at least in the portion of the other zone contiguous to said passageway,
   one of said zones containing a cell-agglutinating reagent immovably adhered to at least one of (i) said surfaces and (ii) said spacing means, and inlet means permitting the introduction of whole blood into said one zone;
   the other of said zones being adapted to receive plasma from said one zone and containing a detection element including at least one detection reagent specific to the analysis of an analyte of the plasma;
   and meniscus control means associated with said passageway for stopping the liquid meniscus from proceeding into said other zone from said one zone, said control means being configured to permit the plasma to pass into said other zone only when an externally generated pressure is applied to the liquid in an amount sufficient to push the liquid meniscus into said other zone.

28. A device as defined in claim 27, wherein said means for spacing includes sidewall surfaces cooperating with said two surfaces to define said connected zones connected by said passageway, said sidewall surfaces forming in said passageway an energy barrier to meniscus flow such that the meniscus of the liquid stops at said meniscus control means.

29. A device as defined in claim 27, wherein at least one of said two surfaces comprises, in both of said zones, a relatively non-wettable material coated with a surfactant soluble in the liquid and capable of making said surfaces wettable by the liquid.

30. A device as defined in claim 27, wherein said means for spacing includes sidewall surfaces cooperating with said two surfaces to define said transport zones connected by said passageway, said sidewall surfaces and said two surfaces forming said passageway with a length in the direction of liquid flow therethrough no greater than about 0.03 cm.

31. A device as defined in claim 27, and further including a third zone disposed between said two zones and fluidly connected thereto by two of said meniscus control means.

32. A device as defined in claim 31, wherein said detection element comprises detection reagents sufficient to generate a color change proportional to the amount of plasma ammonia as well as the amount of plasma creatinine that are present in the whole blood.

33. A device as defined in claim 27, wherein said spaced-apart distance is effective to induce capillary flow of said introduced liquid at least in the portion of said one zone contiguous to said passageway, and in said other zone.

34. A device as defined in claim 33, wherein said spaced-apart distance of said other zone is less than said spaced-apart distance of said one zone by an amount effective to preferentially attract said liquid in response to said push of the liquid by the pressure, into other zone from said one zone and to confine the attracted liquid within said other zone.

35. A method for interacting with a reagent a material contained in a liquid, comprising the steps of
   (a) filling with liquid a first zone of a device comprising two adjacent zones fluidly connected by a passageway, both of said zones comprising opposed liquid transport surfaces, two of said surfaces being spaced apart a distance that is effective to induce capillary flow of said introduced liquid at least in the portion of said first zone contiguous to said passageway, and in said second zone, at least one of said zones further including said reagent;
   (b) retaining the liquid within said first zone while the reagent interacts with said material; and thereafter,
   (c) applying to the liquid in said first zone an externally generated pressure in an amount sufficient to force the liquid to start flowing under capillary attraction into said second zone, whereby the liquid flows into the second zone.

36. A method of combining together liquid containing a material a portion of which is labeled for detection, and a reagent capable of bonding with said material, and thereafter detecting the amount of labeled material free of said reagent, the method comprising the steps of
   (a) flowing under capillary attraction (i) a liquid containing an unknown amount of unlabeled material, and (ii) a liquid containing a known amount of said labeled material, into a first zone of a device comprising two adjacent zones fluidly connected by a passageway, said first zone further including said reagent immobilized therein,
   (b) retaining the liquid within said first zone while the reagent binds with and immobilizes some of said labeled material and said unlabeled material;
   (c) applying to the liquid in said first zone an externally generated pressure in an amount sufficient to force the material that is free of said reagent to start flowing under capillary attraction into said second zone, and
   (d) after the liquid has transferred into said said second zone, detecting the free labeled material in said second zone.

37. A method of combining together for detection liquid containing a material a portion of which is labeled for detection, and a reagent capable of binding said material, the method comprising the steps of
   (a) flowing under capillary attraction an amount of liquid containing (i) an unknown amount of unlabeled material, and (ii) a known amount of said labeled material into a first zone of a device comprising two adjacent zones fluidly connected by a passageway, said first zone further including said reagent immobilized therein,
   (b) retaining the liquid within said first zone while the reagent binds with said labeled material and said unlabeled material;
   (c) applying to the liquid in said first zone an externally generated pressure in an amount sufficient to force the liquid and material free of said reagent to start flowing under capillary attraction into said second zone, and
   (d) after the liquid has transferred into said second zone, detecting the bound, immobilized labeled material in said first zone.

38. A method as defined in claim 36 or 37, wherein said material is an immunogen found in a biological liquid, and said reagent is the complement of said immunogen.

39. A method for determining the amount of unlabeled material in a liquid, comprising the steps (a), (b) and (c) of claim 36 or 37, followed by the steps of
  (d) comparing the amount of labeled material detected in said zone against said known amount, and
  (e) calculating the amount of unknown, unlabeled material that competed with the labeled material for said reagent.

40. A method for determining the amount of an analyte of whole blood in a test device comprising two opposed transport surfaces providing at least two transport zones fluidly connected by a passageway, the first of said zones containing a cell-agglutinating reagent that is incapable of moving out of said first zone, and the second of said zones containing at least one detection reagent specific to said analyte; the method comprising the steps of
  (a) flowing under capillary attraction a quantity of whole blood into the first of said zones;
  (b) retaining said quantity of whole blood in said first zone a length of time sufficient to cause blood cells to bind to said cell-agglutinating reagent and thus to separate from the blood plasma;
  (c) applying to the zone containing the plasma an externally generated pressure in an amount sufficient to force the plasma, but not the cells, to flow under capillary attraction into the second of said zones, and
  (d) detecting within said second zone a radiometric change resulting from the interaction between said at least one detection reagent and said analyte.

41. A method as defined in claim 40, and further including a third zone disposed between and fluidly connected to said two zones, said third zone containing a gas-releasing reagent, and
  wherein prior to step (c), the method comprises the additional step of
  (b') applying to the zone containing the liquid an externally generated pressure in an amount sufficient to force the plasma to flow into said third zone, so that gas is released from the plasma before said step (c).

42. In a reaction vessel comprising wall means forming first and second liquid receiving zones, means permitting the introduction of liquid into the first zone, and connecting passageway means for the passage of liquid from the first zone to the second, the improvement wherein
  said wall means forming said zones are spaced apart a distance that induces capillary flow of liquid at least in the portion of the first zone contiguous to said passageway means, and in said second zone, and
  said passageway means includes means for controlling the meniscus forming the leading edge of the capillary flow so as, first, to halt the passage of liquid into said second zone and, second, to permit flow of liquid into said second zone only when sufficient pressure other than that caused by the hydrostatic head of the liquid is subsequently applied to the liquid that has filled said first zone.

* * * * *